United States Patent [19]

Croci et al.

[11] 4,272,438
[45] Jun. 9, 1981

[54] MANUFACTURE OF SEMI-SYNTHETIC PENICILLIN ANTIBIOTICS

[75] Inventors: Marco Croci; Gennaro Maruzzelli, both of Milan, Italy

[73] Assignee: Glaxo Group Limited, London, England

[21] Appl. No.: 79,939

[22] Filed: Sep. 28, 1979

[30] Foreign Application Priority Data

Oct. 6, 1978 [GB] United Kingdom ............... 39599/78

[51] Int. Cl.³ .......................................... C07D 499/12
[52] U.S. Cl. .................................................. 260/239.1
[58] Field of Search ..................................... 260/239.1

[56] References Cited

U.S. PATENT DOCUMENTS 4,181,656  1/1980  Croci et al. .................. 260/239.1
4,182,709  1/1980  Croci et al. .................. 260/239.1

Primary Examiner—Natalie Trousof
Assistant Examiner—Vera C. Clarke
Attorney, Agent, or Firm—Bacon & Thomas

[57] ABSTRACT

Improvements in or relating to the manufacture of semi-synthetic penicillin antibiotics are described. More particularly an improved process for the preparation of a 6β-acylamino penicillanic acid antibiotic product is described in which 6β-aminopenicillanic acid (6-APA) is reacted in an inert solvent with a silylating agent to form a silylated compound of formula (I)

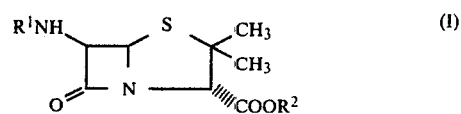

wherein $R^1$ represents a hydrogen atom or a tri($C_{1-6}$ alkyl)silyl group, and $R^2$ represents a tri($C_{1-6}$alkyl)silyl group and the compound of formula (I) is thereafter contacted with an acyl chloride or protected acyl chloride corresponding to the desired 6β-acylamino group, the silyl groups are cleaved and the desired antibiotic product is recovered, silylation being effected using a tri($C_{1-6}$alkyl) silylurea or tri($C_{1-6}$alkyl) halosilane and the compound of formula (I) produced being reacted without intermediate isolation with the acyl chloride or protected acyl chloride, wherein acylation is effected in the presence of a hydrogen halide acceptor mixture comprising in excess of 0.15 and preferably up to 3.00 moles of urea per mole of 6-APA; in excess of 0.15, and preferably up to 1.30 moles of bis-tri-($C_{1-6}$alkyl)-silylurea per mole of 6-APA; and in excess of 0.25, and preferably up to 3.30 moles of tri-($C_{1-6}$alkyl)-ammonium halide per mole of 6-APA.

The process is especially useful for the preparation of ampicillin and amoxycillin in high yield and high purity.

19 Claims, No Drawings

MANUFACTURE OF SEMI-SYNTHETIC PENICILLIN ANTIBIOTICS

This invention relates to improvements in or relating to the manufacture of semi-synthetic penicillin antibiotics.

In German OLS No. 2701407, we have described a process for preparing semi-synthetic penicillin antibiotics by condensing the appropriate acyl chloride with silylated 6β-aminopenicillanic acid (6-APA) in the presence, as hydrogen halide acceptor, of an amide. Included as amides which may be used are various substituted ureas though the yields obtained using them do not match the yields obtained using other amides, e.g. acetamide. Although the process itself is valuable in providing penicillin antibiotics in high purity and in good yield, there is concern about the use of simple amides in such processes because of possible toxicity, and there is need for an alternative high yielding process providing products in a high state of purity.

We have now discovered rather surprisingly, that if a particular combination of components which act as a hydrogen halide acceptor mixture is employed during the acylation reaction, in particular a mixture employing urea, a silylated urea and a trialkylammonium halide, the yields are greatly improved and attain and frequently exceed the high levels achieved by the use of otherwise more toxic, more undesirable and more expensive amides. Furthermore, no traces of any toxic contaminating bases that have previously been used as hydrogen halide acceptors appear in the final products and this considerable advantage is achieved without the need for lengthy and costly purification steps.

According to the invention, therefore, there is provided a process for the manufacture of a 6β-acylamino penicillanic acid antibiotic product in which 6β-aminopenicillanic acid (6-APA) is reacted in an inert solvent with a silylating agent to form a silylated compound of formula (I)

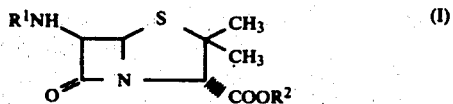

wherein $R^1$ represents a hydrogen atom or a tri($C_{1-6}$ alkyl)silyl group, and $R^2$ represents a tri($C_{1-6}$alkyl)silyl group and the compound of formula (I) is thereafter contacted with an acyl chloride or protected acyl chloride corresponding to the desired 6β-acylamino group, the silyl groups are cleaved and the desired antibiotic product is recovered, silylation being effected using a tri($C_{1-6}$alkyl) silylurea or tri($C_{1-6}$alkyl) halosilane and the compound of formula (I) produced being reacted without intermediate isolation with the acyl chloride or protected acyl chloride, wherein acylation is effected in the presence of a hydrogen halide acceptor mixture comprising in excess of 0.15 and preferably up to 3.00 moles of urea per mole of 6-APA; in excess of 0.15, and preferably up to 1.30 moles of bis-tri-($C_{1-6}$ alkyl)-silylurea per mole of 6-APA; and in excess of 0.25, and preferably up to 3.30 moles of tri-($C_{1-6}$alkyl)-ammonium halide per mole of 6-APA.

Silylation of the 6-APA will generally result in silylation of substantially 100% of the carboxyl group and in excess of 60% of the amino group. However, we believe that silylation of the amino group is very close to 100% when there is an excess of silylating agent in equilibrium with 6-APA.

It is preferred that acylation is effected in the presence of from 0.30 to 2.60 moles of urea per mole of 6-APA; from 0.30 to 0.90 moles of bis-tri-($C_{1-6}$alkyl) silyl urea per mole of 6-APA; and from 0.50 to 3.00 moles of tri-($C_{1-6}$alkyl)ammonium halide.

The order in which the various components of the hydrogen halide acceptor mixture are added to the reaction so that they will be present during the acylation step is in no way critical. For example, the bis-tri($C_{1-6}$alkyl)silylurea and the tri-($C_{1-6}$alkyl)ammonium halide may be added to the reaction prior to the silylation step. Alternatively, but more conveniently, the bis-tri($C_{1-6}$alkyl)silylurea and tri($C_{1-6}$alkyl)ammonium halide will be formed in situ before the acylation step by reaction of urea with a silylating agent and by combination of a tri-($C_{1-6}$alkyl)amine with the hydrohalic acid formed during a silylation usig a tri($C_{1-6}$alkyl) halosilane, preferably during the silylation of 6-APA.

Formation of the bis-tri($C_{1-6}$alkyl)silylurea and tri($C_{1-6}$alkyl) ammonium halide in situ will generally be carried out at a temperature e.g. from +30° to +60° C., for example about 40° C., by reaction of urea with a tri-($C_{1-6}$alkyl)halosilane in the presence of a tri-($C_{1-6}$alkyl)amine base. The reaction time will vary according to the temperature employed, but will generally be complete within a few hours. A particularly useful solvent for this reaction is methylene chloride.

To determine the exact amount of the different starting materials when one or more of the components of the hydrogen halide acceptor mixture is being formed in situ, it is necessary to estimate the amount of the silylating agent(s) consumed in the silylation of 6-APA. When silylation of 6-APA is carried out using a bis-tri-($C_{1-6}$alkyl) silylurea this reagent will desirably be employed in an amount of more than 1.15, preferably 1.30–1.45 moles per mole of 6-APA, in order that 6-APA be silylated and the minimum required amount of bis-tri($C_{1-6}$alkyl) silylurea will remain for the acylation reaction. In this embodiment more than 0.25 moles of tri-($C_{1-6}$alkyl) ammonium halide should be added at some point before the acylation reaction involving the acyl halide and silylated 6-APA.

The tri($C_{1-6}$alkyl) ammonium halide will most desirably be triethylammonium chloride though any tri($C_{1-6}$alkyl)-ammonium halide, e.g. chloride or bromide may be used. Alternatively, the silylation of 6-APA may be carried out using a tri-($C_{1-6}$alkyl) halosilane and a tri-($C_{1-6}$alkyl)amine. In this embodiment, each of these reagents should be employed in an amount of at least 2.3 moles, preferably 2.5–2.7 moles per mole of 6-APA, and sufficient urea should be present throughout the silylation reaction in order that some of it will undergo silylation to give at least the minimum required amount of a silylated urea, and leave at least the minimum required amount of urea itself, in equilibrium with the other components of the hydrogen halide acceptor mixture.

The tri($C_{1-6}$alkyl) halosilane will most advantageously be trimethylchlorosilane in view of its low cost. The tri($C_{1-6}$alkyl)amine will most preferably be triethylamine.

The reason for the remarkable improvement in yield as a result of the balance in quantities between the trialkylammonium salt, the urea and the silylated urea in the reaction mixture is not fully understood but is believed to be a consequence of an equilibrium existing between the trialkyl ammonium salt, the silylated urea and the urea itself, which in combination act as a hydrogen halide acceptor mixture.

In a preferred embodiment of this invention, the 6-APA and urea are simultaneously silylated by adding the required amounts of trimethylchlorosilane and triethylamine to a stirred suspension thereof in an anhydrous aprotic organic solvent. These compounds are generally added with agitation or stirring over a period of up to a few hours. The solvent employed is most preferably methylene chloride. The preferred volume of methylene chloride is from 6 to 20 ml per gram weight of 6-APA, but it is not critical.

The reagents can be added to the stirred reaction medium in any desired sequence, at a temperature between e.g. −30° up to boiling point of the mixture which will be around +42° C. It is preferred to mix all the reagents at a temperature of from 0° C. to +20° C. The number of moles of the trimethylchlorosilane will desirably be more than or at least the same as the number of moles of triethylamine to avoid the presence of a substantial amount of free triethylamine during the acylation reaction. Indeed, trialkylamines are well known to produce undesired by-products, especially when the acyl halide contains an amino group protected by a hydrohalide (e.g. D(−) phenylglycylchloride hydrochloride in the synthesis of ampicillin). From 2.3 to 3.2 moles of triethylamine, preferably 2.5 to 2.7 moles, and from 2.3 to 3.2 moles of trimethylchlorosilane, preferably 2.5 to 2.7 moles will generally be added per mole of 6-APA. There will also generally be added from 0.5 to 3.0 moles of urea, preferably 1.0 to 2.0 moles per mole of 6-APA. An advantage of this invention is that no special purity is required for the reagents and for the solvent.

The silylation of the 6-APA and of the urea is desirably carried out by stirring the reaction mixture at a temperature which depends on the nature of the solvent. When methylene chloride is employed, the required reactions are generally complete within four hours at temperatures beteen +30° C. and the boiling point of the mixture, e.g. about +42° C. The same reaction times and temperatures may be suitable if an alternative embodiment of this invention is effected, i.e. the silylation of 6-APA with the required amount of bis-trimethylsilyl urea with the addition of tri-($C_{1-6}$alkyl) ammonium halide.

In general, the tri($C_{1-6}$alkyl) ammonium halide is preferably present throughout all of the silylation and acylation reactions. Both embodiments of the invention are able to produce in situ a mixture which will act as a hydrogen halide acceptor in the subsequent acylation step; they are also able to achieve rapidly the solubility equilibria for all the three components and for all the intermediates or complexes they may form.

Once the silylation of 6-APA and urea has been effected, the suspension will be preferably cooled to from +10° C. to −35° C., desirably from −5° to −25° C., prior to addition of acyl halide. It is an advantageous feature of the present invention that no further hydrogen halide acceptor needs to be added to the reaction mixture before the acylation step. Addition of the acyl halide may be effected portionwise, the temperature being maintained e.g. around or below −5° C. We generally prefer to employ an approximately stoichiometric amount of acyl halide e.g. up 1.1. equivalents, advantageously 1.0 equivalent, relative to the quantity of silylated 6-APA.

The acyl halide employed is chosen according to the nature of the desired 6β-acylamino group. When the latter contains reactive groups it may be necessary to protect these during the process of the invention. Thus, in manufacturing ampicillin, the α-amino group of the D(−) phenylglycylchloride may be protected by, for example, hydrochloric acid. The process according to the present invention is applicable to the manufacture of ampicillin, amoxycillin, methicillin, oxacillin, cloxacillin, dicloxacillin, flucloxacillin, α-carboxyesters of carbenicillin, and in general to the manufacture of any penicillin the synthesis of which can be made by acylation of 6-APA with an acyl halide, and the nature of which is well defined in existing literature.

Once all the acyl halide has been added, temperature control is desirably maintained throughout the acylation reaction, which proceeds comparatively rapidly and should normally be complete within 30 minutes to 3 hours, e.g. about one and a half hours.

After completion of the acylation reaction, for example as evidenced by consumption of the starting materials, the resulting mixture may be treated with a compound containing active hydrogen, e.g. water, acidified or basified water, an alcohol or a phenol, to remove any silyl groups present in the penicillin reaction product. Water is the preferred desilylating agent for this purpose.

When ampicillin, amoxycillin or other zwitterionic penicillins are the desired penicillin antibiotics, they may be precipitated e.g. by adjusting the pH of the water-diluted reaction mixture to the isoelectric point with a base, and the precipitate may be recovered and dried by conventional means. When isoxazolic penicillins or other acidic penicillins are the desired penicillin antibiotics, they may be isolated by discarding the aqueous acidic layer, optionally drying the organic layer containing the penicillin in the acidic form, and then precipitating it in the alkaline salt form, by exchange with a suitable salt for instance sodium or potassium 2-ethyl-hexanoate.

The process according to this invention is particularly applicable to the manufacture of ampicillin, 6-(D-2-amino-2-phenylacetamido)-2,2-dimethylpenam-3-carboxylic acid, and amoxycillin, 6-(D-2-amino-2-(4-hydroxy)phenylacetamido)-2,2-dimethylpenam-3-carboxylic acid, e.g. in their trihydrate forms.

The invention will now be more particularly described in the following Examples which should not be construed as limiting the invention.

In all the Examples that follow in which the amount of one or more of the reagents is varied, the figures given refer to the amounts added and should not be confused with the amounts of each component of the hydrogen halide acceptor mixture present at the start of the acylation reaction. Also, the percentage yields given are not corrected for the purities of the 6β-aminopenicillanic acid starting material or the antibiotic product.

In the Examples, the nature and purity of the end products were determined by standard techniques, including polarimetry and spectrophotometry. A description of the spectrophotometric method used to assay the ampicillin and amoxycillin may be found in British Pharmacopoeia, (1973, H.M.S.O.) on page 30, and in the same reference an account of the acidimetric assay used to assay cloxacillin, dicloxacillin and flucloxacillin is given on page 81; a description of the microbiological assay technique for ampicillin is given in British Pharmacopoeia (1973 H.M.S.O.) on pages 102–104 of the Appendix.

The water contents were determined by Karl Fisher analysis or by measuring the weight loss on heating to form the anhydrous compound.

The purity of the antibiotic products is given after allowance has been made for the water (hydrate) content of the product obtained.

The specific rotation of ampicillin trihydrate is given as $[\alpha]_D^{20} = +280°$ to $+305°$ (c=0.25 in water) in the British Pharmacopoeia (1973 H.M.S.O. Addendum 1978); the specific rotation of amoxycillin trihydrate is given as $[\alpha]_D^{20} = +290°$ to $+310°$ (c=0.2 in water) in the same publication (Addendum 1975); and the specific rotation of cloxacillin as sodium salt is given as $[\alpha]_D^{20} = +156°$ C. to $+164°$ (c=1 in water) in the British Pharmaceopoeia (1973, H.M.S.O.). That of dicloxacillin as sodium salt is given as $[\alpha]_D^{24} = +135°$ (c=0.4 in water) in the Merck Index (8th Edition).

then dried in an oven to yield 70.4 g (87.4% of the theoretical amount), of ampicillin trihydrate as a white, crystalline powder.

| Water content | 13.7% |
|---|---|
| Specific rotation | +293° on the anhydrous basis |
| Spectrophotometric assay | 97.9% on the anhydrous basis |
| Microbiological assay | 97.6% on the anhydrous basis |

EXAMPLE 2

Preparation of ampicillin trihydrate (i) When the procedure of Example 1 was repeated with amounts of urea ranging from 0.50 to 3.00 moles per mole of 6-amino penicillanic acid (6-APA) the following results were obtained:

| | UREA | | AMPICILLIN TRIHYDRATE | | | | | |
|---|---|---|---|---|---|---|---|---|
| | MOLES PER MOLE OF 6 APA | GRAMS PER 43.2 G OF 6 APA | YIELD (GRAMS PER 43.2 G OF 6 APA | YIELD (% OF THEORETICAL) | ASSAY[1] (% ON ANHYD. BASIS) | SPECIF. ROTAT. (°) | WATER CONTENT (°) | ASSAY[2] (% ON ANHYD. BASIS) |
| (a) | 0.50 | 6.0 | 68.4 | 84.9 | 97.9 | 295 | 13.3 | |
| (b) | 0.80 | 9.6 | 69.5 | 86.2 | 98.1 | 297 | 13.4 | |
| (c) | 1.00 | 12.0 | 70.0 | 86.9 | | 294 | 13.1 | 98.5 |
| (d) | 1.20 | 14.4 | 70.2 | 87.1 | 97.4 | 294 | 13.6 | |
| (e) | 1.50 | 18.0 | 70.4 | 87.4 | 97.9 | 293 | 13.7 | 97.6 |
| (f) | 1.80 | 21.6 | 69.4 | 86.1 | | 298 | 13.1 | |
| (g) | 2.00 | 24.0 | 69.4 | 86.1 | 99.3 | 297 | 13.7 | |
| (h) | 3.00 | 36.0 | 68.8 | 85.4 | | 294 | 13.3 | |

[1]The assay carried out was spectrophotometric
[2]The assay carried out was microbiological

EXAMPLE 1

Preparation of ampicillin trihydrate 52.6 g (0.520 moles; purity 100%) of triethylamine were added to a stirred suspension of 18.0 g (0.300 moles; purity 100%) of urea and 43.2 g (0.197 moles; purity 98.4%) of 6-aminopenicillanic acid in 390 ml of methylene chloride at 20° C. Then 59.5 g (0.520 moles; purity 95.0%) of trimethylchlorosilane were added over 15 minutes, maintaining the temperature at 20° C. After 30 minutes of stirring, the temperature was raised to +40° C., and maintained for 60 minutes. The white suspension was cooled to −25° C., and 43.2 g (0.197 moles; purity 93.9%) of D(−)α-phenylglycylchloride were added; the temperature was allowed to increase to −5° C. and held at this temperature for a total time of 90 minutes. 450 ml of water were added and ampicillin trihydrate was precipitated by adjusting the pH to 4.5 with dilute ammonium hydroxide. After stirring for an hour at 10°/15° C. the product was filtered off and washed with 150 ml of water and 375 ml of acetone and (ii) When the same process was repeated without any urea, a yield of 51.0 g of ampicillin trihydrate per 43.2 g of 6-APA (63.3% of theoretical) was obtained iii) When the same process was repeated using 0.30 moles of urea per mole of 6 APA (3.6 grams per 43.2 grams of 6-APA), the yield obtained was 64.5 grams of ampicillin trihydrate (80.0% of theoretical), Spectrophotometric Assay 97.5% on the anhydrous basis, specific rotation +293° on the anhydrous basis, water content 13.5%

EXAMPLE 3

Preparation of ampicillin trihydrate

When the procedure of Example 1 was repeated except that 1.50 moles of urea per mole of 6-APA were added to the reaction mixture after the silylation step, at −25° C., and immediately before the acylation step, the yield obtained was significantly lower than that obtained with the same amount of urea added before the silylation step.

| | UREA | | AMPICILLIN TRIHYDRATE | | | | |
|---|---|---|---|---|---|---|---|
| | MOLES PER MOLE OF 6 APA | GRAMS PER 43.2 G OF 6 APA | YIELD (GRAMS PER 43.2 G OF 6 APA | YIELD (% OF THEORETICAL) | ASSAY (% ON ANHYD. BASIS) | SPECIF. ROTAT. (°) | WATER CONTENT (%) |
| (a) | 1.50 | 18.0 | 70.4 | 87.4 | 97.9 | 293 | 13.7 |

-continued

| | UREA | | AMPICILLIN TRIHYDRATE | | | | |
|---|---|---|---|---|---|---|---|
| | MOLES PER MOLE OF 6 APA | GRAMS PER 43.2 G OF 6 APA | YIELD (GRAMS PER 43.2 G OF 6 APA | YIELD (% OF THEORE- TICAL) | ASSAY (% ON ANHYD. BASIS) | SPECIF. ROTAT. (°) | WATER CONTENT (%) |
| (b) | 1.50 φ | 18.0 φ | 58.0 | 72.0 | + | + | + |

+ scarcely soluble product, not assayed.
φ added after the silylation step.

The assay carried out was spectrophotometric.

EXAMPLE 4

Preparation of ampicillin trihydrate

When the procedure of Example 1 was repeated using varying amounts of urea, triethylamine (TEA) and trimethylchlorosilane (TMCS), the following results were obtained:

| | MOLES PER MOLE OF 6-APA | | | AMPICILLIN TRIHYDRATE | | | | |
|---|---|---|---|---|---|---|---|---|
| | UREA | TEA | TMCS | YIELD (GRAMS PER 43.2 G OF 6-APA | YIELD (% OF THEORE- TICAL) | ASSAY (% ON ANHYD. BASIS) | SPECIF. ROTAT. (°) | WATER CON- TENT (%) |
| (a) | 1.5 | 2.3 | 2.3 | 68.0 | 84.4 | | 293 | 13.2 |
| (b) | 1.5 | 2.6 | 2.6 | 70.4 | 87.4 | 97.9 | 293 | 13.7 |
| (c) | 1.5 | 2.9 | 2.9 | 69.5 | 86.2 | | 295 | 13.1 |
| (d) | 3.0 | 2.3 | 2.3 | 66.0 | 81.9 | | 289 | 13.8 |
| (e) | 3.0 | 2.6 | 2.6 | 68.6 | 85.4 | | 294 | 13.3 |
| (f) | 3.0 | 2.9 | 2.9 | 69.8 | 86.6 | | 286 | 13.4 |
| (g) | 3.0 | 3.2 | 3.2 | 68.1 | 84.5 | | 289 | 13.1 |

The assay carried out was spectrophotometric (i) When the same procedure was repeated using 1.5 moles of urea per mole of 6-APA, and 2.0 moles per mole of 6-APA of each of TEA and TMCS, 64.5 grams of ampicillin trihydrate per 43.2 grams of 6-APA were obtained (80.0% of theoretical). Spectrophotometric Assay 98.6% on the anhydrous basis; specific rotation +297° on the anhydrous basis; water content 13.6%. (ii) When the same procedure was repeated as in (i) above but using 3.0 moles of urea per mole of 6-APA, a yield of 60.6 grams of ampicillin trihydrate per 43.2 grams of 6-APA (75.2% of theoretical) was obtained. Specific rotation +290° on the anhydrous basis, water content 13.4%.

EXAMPLE 5

Preparation of ampicillin trihydrate 40.5 g (0.400 moles: purity 100%) of triethylamine (TEA) was added to a stirred suspension of 18.0 g (0.300 moles: purity 100%) of urea and 43.2 g (0.197 moles: purity 98.4%) of 6-APA in 390 ml of methylene chloride at 20° C. Then 45.4 g (0.400 moles: purity 95.8%) of trimethylchlorosilane (TMCS) were added over 15 minutes, maintaining the temperature at 20° C. Then 12.9 g (0.060 moles; purity 95%) of bis-trimethylsilylurea (BSU) were added; after 30 minutes of stirring, the temperature was raised to 40° C. and the reaction was continued and completed according to the procedure of Example 1. Yield: 70.6 g of ampicillin trihydrate (87.6% of the theoretical amount), as a white, crystalline powder.

| Water content | 13.4 % |
|---|---|
| Specific rotation | + 295° on the anhydrous basis. |

EXAMPLE 6

Preparation of ampicillin trihydrate

When the procedure of Example 5 was repeated but the amount of BSU was varied in the range 0.15 to 1.00 moles per mole of 6-APA, the following results were obtained:

| | MOLES PER MOLES OF 6-APA | | | | AMPICILLIN TRIHYDRATE | | | |
|---|---|---|---|---|---|---|---|---|
| | UREA | TEA | TMCS | BSU | YIELD (GRAMS PER 43.2 G OF 6-APA) | YIELD (% OF THEORE- TICAL) | SPECIF. ROTAT. (°) | WATER CONT. (%) |
| (a) | 1.5 | 2.0 | 2.0 | 0.15 | 68.0 | 84.4 | 295 | 13.2 |
| (b) | 1.5 | 2.0 | 2.0 | 0.30 | 70.6 | 87.6 | 295 | 13.4 |
| (c) | 1.5 | 2.0 | 2.0 | 0.45 | 70.9 | 88.0 | 293 | 13.3 |
| (d) | 1.5 | 2.0 | 2.0 | 0.60 | 70.0 | 86.9 | 294 | 13.3 |
| (e) | 1.5 | 2.0 | 2.0 | 1.00 | 68.3 | 84.7 | 294 | 13.5 |

These results should also be compared with the yield obtained in Example 4 (i) in which no BSU is added.

EXAMPLE 7

Preparation of ampicillin trihydrate (i) When the procedure of Example 5 was repeated but 0.30 moles of BSU per mole of 6-APA was added to the reaction mixture after the silylation step, at $-25°$ C., and immediately before the acylation step, the yield obtained was 70.0 g of ampicillin trihydrate (86.9% of the theoretical amount). Water content 13.3%; specific rotation $+295°$ on the anhydrous basis.

(ii) When the procedure of Example 5 was repeated but the urea was added after the silylation step, at $-25°$ C., immediately before the acylation step, the yield obtained was 65.8 g (81.6% of the theoretical amount). Water content 13.6%; specific rotation $+292°$ on the anhydrous basis.

(iii) When the procedure of Example 5 was repeated but the BSU and urea were both added to the reaction mixture after the silylation step, at $-25°$ C., immediately before the acylation step, the yield obtained was 65.9 g (81.8% of the theoretical amount). Water content 13.6%; specific rotation $+292°$ on the anhydrous basis.

(iv) When the procedure of Example 5 was repeated but no urea was added at all, the yield obtained was 62.5 g (77.5% of the theoretical amount). Water content 13.3%; specific rotation $+289°$ on the anhydrous basis.

EXAMPLE 8

Preparation of ampicillin trihydrate 28.0 g (0.130 moles; purity 95%) of bis-trimethylsilylurea (BSU) were added to a stirred suspension of 6.9 g (0.050 moles; purity 100%) of triethylammonium chloride (TEC) and 21.6 g (0.098 moles; purity 98.4%) of 6-APA in 195 ml of methylene chloride at 20° C. The temperature was raised to reflux temperature and maintained at this value for 120 minutes. The white suspension was cooled at $-25°$ C., and the reaction was completed according to the procedure of Example 1. Yield: 70.4 of ampicillin trihydrate (87.4% of the theoretical amount), as a white, crystalline powder. Water content 13.1%; specific rotation $+295°$ on the anhydrous basis.

EXAMPLE 9

Preparation of ampicillin trihydrate

When the procedure of Example 8 was repeated but the amount of BSU was varied in the range 1.15 to 1.60 moles per mole of 6-APA, the following results were obtained:

|     | MOLES PER MOLE OF 6-APA | | AMPICILLIN TRIHYDRATE | | | |
| --- | --- | --- | --- | --- | --- | --- |
|     | TEC | BSU | YIELD (GRAMS PER 43.2 G OF 6-APA) | YIELD (% OF THEORETICAL) | SPECIF. ROTAT. (°) | WATER CONTENT (%) |
| (a) | 0.50 | 1.15 | 67.0 | 83.1 | 295 | 13.3 |
| (b) | 0.50 | 1.30 | 70.4 | 87.4 | 295 | 13.1 |
| (c) | 0.50 | 1.45 | 69.8 | 86.6 | 293 | 13.5 |
| (d) | 0.50 | 1.60 | 68.0 | 84.4 | 294 | 13.5 |

(i) When this procedure was repeated using only 1.00 mole of BSU per mole of 6-APA, a yield of 61.6 grams of ampicillin trihydrate per 43.2 grams of 6-APA (76.4% of theoretical) was obtained. Specific rotation $+294°$ on the anhydrous basis, water content 13.5%.

EXAMPLE 10

Preparation of ampicillin trihydrate

When the procedure of Example 8 was repeated but the amount of TEC was varied in the range 0.25 to 2.60 moles per mole of 6-APA, the following results were obtained:

|     | MOLES PER MOLE OF 6-APA | | AMPICILLIN TRIHYDRATE | | | |
| --- | --- | --- | --- | --- | --- | --- |
|     | BSU | TEC | YIELD (GRAMS PER 43.2 G OF 6-APA) | YIELD (% OF THEORETICAL) | SPECIF. ROTAT. (°) | WATER CONTENT (%) |
| (a) | 1.30 | 0.25 | 67.0 | 83.1 | 294 | 13.5 |
| (b) | 1.30 | 0.50 | 70.4 | 87.4 | 295 | 13.1 |
| (c) | 1.30 | 2.60 | 66.8 | 82.9 | 294 | 13.2 |
| (d) | 1.60 | 0.25 | 67.6 | 83.9 | 293 | 13.6 |
| (e) | 1.60 | 0.50 | 68.0 | 84.4 | 294 | 13.5 |

(i) When the above procedure was repeated using no TEC at all, 50.0 grams of ampicillin trihydrate per 43.2 grams of 6-APA were obtained (62.0% of theoretical). Specific rotation $+288°$ on the anhydrous basis. Water content 13.1%.

EXAMPLE 11

Preparation of ampicillin trihydrate

When the procedure of Example 8 was repeated but 0.50 moles of TEC per mole of 6-APA was added to the reaction mixture after the silylation step, at $-25°$ C., immediately before the acylation step, the yield obtained was 68.4 g (84.9% of the theoretical amount). Water content 13.3%; specific rotation $+295°$ on the anhydrous basis.

EXAMPLE 12

Preparation of ampicillin trihydrate 56.0 g (0.260 moles; purity 95%) of BSU were added to a stirred suspension of 12.0 g (0.200 moles; purity 100%) of urea 13.8 g (0.100 moles; purity 100%) of TEC and 43.2 g (0.197 moles; purity 98.4%) of 6-APA in 390 ml of methylene chloride at 20° C. The temperature was raised to reflux temperature and maintained at this value for 120 minutes, whilst stirring was continued. The white suspension was cooled to $-25°$ C., and the reaction was completed according to the procedure of Example 1. Yield: 71.0 g (88.1% of the theoretical amount), of ampicillin trihydrate as a white, crystalline powder. Water content 13.4%; specific rotation $+297°$ on the anhydrous basis.

EXAMPLE 13

Preparation of ampicillin trihydrate (i) When the procedure of Example 12 was repeated but TEC was omitted, the yield obtained was 54.0 g (67.0%) Water content 13.7%; specific rotation $+291°$ on the anhydrous basis.

(ii) When urea was omitted in the procedure of Example 12 the yield obtained was 70.4 g (87.4%). Water content 13.1%; specific rotation $+295°$ on the anhydrous basis.

(iii) When both TEC and urea were omitted in the procedure of Example 12, the yield obtained was 50.0 g (62.0%). Water content 13.1%; specific rotation +288° on the anhydrous basis.

EXAMPLE 14

Preparation of amoxycillin trihydrate 52.6 g (0.520 moles; purity 100%) of triethylamine were added to a stirred suspension of 18.0 g (0.300 moles; purity 100%) of urea and 43.2 g (0.197 moles; purity 98.3%) of 6-aminopenicillanic acid in 430 ml of methylene chloride at 20° C. Then 60.9 g (0.540 moles; purity 96.1%) of trimethylchlorosilane were added over 15 minutes, maintaining the temperature at 20° C. After 30 minutes of stirring, the temperature was raised to 40° C. and held for 60 minutes. The white suspension was cooled to −25° C., and 57.0 g (0.196 moles; purity 76.3%) of D(−) α-(4-hydroxy)phenylglycylchloride hydrochloride were added; the temperature was allowed to increase to −10° C. and held at this value for a total time of 90 minutes. 700 ml of water were added, the organic layer was discarded and amoxycillin trihydrate was precipitated by adjusting the pH of the aqueous layer to 4.5 with dilute ammonium hydroxide. After stirring for an hour at 10/15° C. the product was filtered off and washed with 150 ml of water and 375 ml of acetone and then dried in an oven at 40° C. to yield 70.0 g of amoxycillin trihydrate (83.5% of the theoretical amount), as a white, crystalline powder.

| | |
|---|---|
| Water content | 13.0% |
| Specific rotation | +302° on the anhydrous basis |
| Spectrophotometric assay | 98.5% on the anhydrous basis |
| Microbiological assay | 100.0% on the anhydrous basis |

EXAMPLE 15

Preparation of amoxycillin trihydrate 34.4 g (0.160 moles; purity 95%) of bis-trimethylsilyl urea were added to a stirred suspension of 5.5 g (0.040 moles; purity 100%) of triethylammonium chloride (TEC) and 21.6 g (0.098 moles; purity 98.3%) of 6-aminopenicillanic acid in 175 ml of methylene chloride at 20° C. The temperature was raised to reflux and maintained at this value for 120 minutes. The white suspension was cooled at −25° C., and 26.6 g (0.098 moles; purity 81.8%) of D(−) α-(4-hydroxy)phenylglycylchloride hydrochloride were added; the temperature was allowed to increase to −5° C. and held at this value for a total time of 90 minutes. 200 ml of water were added, and amoxycillin trihydrate was precipitated by adjusting the pH to 4.5 with dilute ammonium hydroxide. After stirring for an hour at 10/15° C., the product was filtered off and washed with 80 ml of water and 210 ml of acetone and then dried in an oven at 40° C. to yield 36.2 g of amoxycillin trihydrate (86.4% of the theoretical amount), as a white, crystalline powder.

EXAMPLE 16

Preparation of amoxycillin trihydrate

When no TEC was employed in the procedure of Example 15, but an additional amount of 12.0 g (0.200 moles) of urea were added before the acylation step, the yield obtained was only 26.1 g (62.3% of the theoretical value).

EXAMPLE 17

Preparation of sodium dicloxacillin monohydrate 52.6 g (0.520 moles; purity 100%) of triethylamine were added to a stirred suspension of 18.0 g (0.300 moles; purity 100%) of urea and 43.2 g (0.198 moles; purity 99.0%) of 6-aminopenicillanic acid in 390 ml of methylene chloride at 20° C. Then 60.5 g (0.540 moles; purity 97.1%) of trimethylchlorosilane were added over 15 minutes, maintaining the temperature at 20° C. After 30 minutes of stirring, the temperature was raised to 40° C., and held for 60 minutes. The white suspension was cooled to −30° C., and 59.1 g (0.198 moles; purity 97.4%) of 3-(2′,6′-dichlorophenyl)-5-methyl-4-isoxazolyl chloride were added; the temperature was allowed to increase to 0° C. and held at this value for a total time of 130 minutes. The suspension was added to a mixture of 180 ml of water and 390 ml of acetone, pre-cooled at 0° C. The aqueous layer was separated and discarded, and the organic layer was washed with 180 ml of water. The aqueous layer was separated and discarded, and the organic layer was dried over 50 g of anhydrous sodium sulphate. The product was precipitated as sodium salt monohydrate by addition of 0.200 moles of sodium 2-ethyl-hexanoate as a 1 N solution in acetone. The product was filtered off, washed with 450 ml of acetone and dried in an oven at 40° C. to yield 93.0 g of sodium dicloxacillin monohydrate (91.2% of the theoretical amount), as a white, crystalline powder. Water content 3.7%; spectrophotometric assay 98.3% on the anhydrous basis; specific rotation +133° on the anhydrous basis.

EXAMPLE 18

Preparation of α-benzylester of carbenicillin (potassium salt)

52.6 g (0.520 moles; purity 100%) of triethylamine were added to a stirred suspension of 18.0 g (0.300 moles; purity 100%) of urea and 43.2 g (0.193 moles; purity 96.5%) of 6-aminopenicillanic acid in 390 ml of methylene chloride at 20° C. Then 60.5 g (0.540 moles; purity 97.1%) of trimethylchlorosilane were added over 15 minutes, maintaining the temperature at 20° C. After 30 minutes, the temperature was raised to 40° C. and kept for 60 minutes. The white suspension was cooled to −30° C., and 61.5 g (0.200 moles; purity 93.8%) of α-(carboxybenzyl)phenylacetyl chloride were added over 10 minutes; the temperature was allowed to increase to 0° C. and kept at this value for a total time of 130 minutes. The suspension was added to a mixture of 180 ml of water and 390 ml of acetone, precooled at 0° C. The aqueous layer was separated and discarded, and the organic layer was washed with 180 ml of water. The aqueous layer was separated and discarded, and the organic layer was dried over 50 g of anhydrous sodium sulphate. The product was precipitated as potassium salt by addition of 0.300 moles of potassium 2-ethyl-hexanoate as a 1 N solution in acetone. The product was filtered off, washed with 450 ml of acetone and dried in an oven at 40° C. Yield: 65.4 g of α-benzylester of potassium carbenicillin (64.6% of the theoretical amount). Water content: 0.3%: specific rotation +188° on the anhydrous basis.

EXAMPLE 19

Preparation of sodium cloxacillin monohydrate

The procedure of Example 17 was followed except that 51.2 g (0.198 moles, purity 99.0%) of 3-(2'-chlorophenyl)-5-methyl-4-isoxazolyl chloride were employed as the acyl chloride. The yield was 85.6 g of sodium cloxacillin monohydrate (90.0% of the theoretical amount).

EXAMPLE 20

Preparation of ampicillin trihydrate (a) 52.6 g (0.520 moles) of triethylamine were added under stirring to a suspension of 12.0 g (0.200 moles) of urea in 350 ml of methylene chloride. The temperature was increased to +40° C. and addition was made over an hour of 58.7 g (0.540 moles) of trimethylchlorosilane. Under continuous stirring, 43.2 g (0.200 moles) of 6-APA were added and the temperature was held for another hour at +40° C. The suspension was cooled to −25° C., and 43.3 g (0.200 moles; purity 95.0%) of D(−)-α-phenylglycylchloride hydrochloride were added; the temperature was allowed to increase to −5° C. and held at this temperature for a total time of 90 minutes. 450 ml of water were added and ampicillin trihydrate was precipitated by adjusting the pH to 4.5 with dilute ammonium hydroxide. After stirring for an hour at +10°/+15° C. the product was filtered and washed with 2×75 ml of water and 3×125 ml of acetone and then dried at +40° C. to yield 68.6 g (85.1% of the theoretical amount) of ampicillin trihydrate.

| | |
|---|---|
| Water content | 13.8% |
| Specific rotation | +297° on the anhydrous basis |
| Spectrophotometric assay | 99.0% on the anhydrous basis |

(b) When the amount of urea was increased to 18.0 g (0.300 moles) the yield obtained was similar (69.0 g; 85.6%). Water content 13.9%; specific rotation +297°; spectrophotometric assay 98.7%.

EXAMPLE 21

Preparation of amoxycillin trihydrate 46.5 g (0.460 moles) of triethylamine were added under stirring to a suspension of 13.2 g (0.220 moles) of urea in 350 ml of methylene chloride. The temperature was increased to +40° C. and addition was made over an hour of 52.2 g (0.480 moles) of trimethylchlorosilane. Under continuous stirring, 43.2 g (0.200 moles) of 6-APA were added and the temperature was held for another hour at +40° C. The suspension was cooled to −25° C., and 44.4 g (0.200 moles) of D(−)α-(4-hydroxy)phenylglycylchloride hydrochloride were added, and the procedure of Example 20 was then followed to obtain amoxycillin trihydrate. Yield: 66.0 g (78.8% of the theoretical amount).

EXAMPLE 22

Preparation of ampicillin trihydrate (a) 6.9 g (0.050 moles) of triethylamine hydrochloride and 51.0 g (0.250 moles) of N,N'-bis-trimethylsilylurea were added to a suspension of 43.2 g (0.200 moles) of 6-APA in 350 ml of methylene chloride under stirring. The mixture was heated to reflux for two hours and then cooled to −25° C.; 43.3 g (0.200 moles; purity 95.0%) of D(−)-α-phenylglycylchloride hydrochloride were added, and the procedure of Example 20 was then followed to obtain ampicillin trihydrate.

| | |
|---|---|
| Yield | 66.9 g (83.0% of theoretical) |
| Water content | 14.0% |
| Specific rotation | +296° |
| Spectrophotometric assay | 98.3% |

(b) When the triethylamine hydrochloride amount was increased to 68.8 g (0.500 moles) while keeping the other conditions constant, the yield was increased to 68.6 g (85.1% of the theoretical amount). Water content 13.8%; specific rotation +295°; spectrophotometric assay 98.0%.

(c) When triethylamine hydrochloride was not used at all, the yield obtained was 56.6 g (70.2%). The yield was not increased by increasing the amount of bis-trimethylsilylurea to 2 moles per mole of 6-APA.

EXAMPLE 23

Preparation of amoxycillin trihydrate (a) 6.9 g (0.050 moles) of triethylamine hydrochloride and 51.0 g (0.250 moles) of N,N'-bis-trimethylsilylurea were added to a suspension of 43.2 g (0.200 moles) of 6-APA in 350 ml of methylene chloride under stirring. The mixture was heated to reflux for two hours and then cooled to −25° C.; 44.4 g (0.200 moles) of D(−)-α-(4-hydroxy)phenylglycylchloride hydrochloride were added, and the procedure of Example 20 was then followed to obtain amoxycillin trihydrate. Yield: 62.8 g (74.9% of the theoretical amount).

(b) When triethylamine hydrochloride was not used at all, the yield obtained was 50.2 g (59.9%).

EXAMPLE 24

Preparation of sodium dicloxacillin monohydrate 52.5 g (0.520 moles) of triethylamine were added under stirring to a suspension of 24.0 g (0.400 moles) of urea in 350 ml of methylene chloride. The temperature was increased to +40° C. and addition was made over sixty minutes of 58.7 g (0.540 moles) of trimethylchlorosilane. Under continuous stirring, 43.2 g (0.200 moles) of 6-APA were added and the temperature was held for another sixty minutes at +40° C. The suspension was cooled to −25° C. and 58.1 g (0.200 moles) of 3-(2',6'-dichlorophenyl)-5-methyl-4-isoxazolyl chloride were added. The temperature was allowed to increase to 0° C. and was held there for a total time of 60 minutes starting from the addition of the acyl chloride. 175 ml of acetone and 300 ml of water were then added; the phases were separated and the aqueous phase was discarded; the organic phase was again washed with 300 ml of water, and the aqueous phase was discarded. The organic phase was treated for 30 minutes with anhydrous sodium sulphate; the drying agent was then filtered, and washed with 175 ml of acetone which was combined with the main organic phase. An additional portion of 350 ml of acetone was added to the organic phase, and the sodium salt monohydrate of dicloxacillin was then precipitated by adding to the combined organic phases 200 ml of a 1 N solution of sodium 2-ethylhexanoate in acetone. After 60 minutes stirring the crystalline white solid was filtered, and then washed with 3×150 ml of acetone; drying was in vacuum oven at +35°/+40° C. The yield was 81.8 g (80.2% of the theoretical amount).

EXAMPLE 25

Preparation of sodium cloxacillin monohydrate

The procedure of Example 24 was repeated, except that 51.2 g (0.200 moles) of 3-(2'-chlorophenyl)-5-methyl-4-isoxazolyl chloride were used as the acyl chloride in the condensation step. The yield was 76.1 g (79.9% of the theoretical amount).

| Water content: | 3.8% | |
| --- | --- | --- |
| Specific rotation: | +133° | on the anhydrous basis |
| Assay: | 99.4% | as sodium salt monohydrate. |

| Water content: | 4.0% | |
| --- | --- | --- |
| Specific rotation: | +160° | on the anhydrous basis |
| Assay: | 98.0% | as sodium salt monohydrate |

EXAMPLE 26

Preparation of sodium flucloxacillin monohydrate

The procedure of Example 24 was repeated, except that 54.8 g (0.200 moles) of 3-(2'-chloro-6'-fluorophenyl)-5-methyl-4-isoxazolyl chloride were used as acyl chloride in the condensation step, and that all the amounts of acetone indicated in Example 24 were reduced to one fifth. The yield was 72.5 g (73.4% of the theoretical amount).

| Water content: | 5.5% | |
| --- | --- | --- |
| Specific rotation: | +163° | on the anhydrous basis |
| Assay: | 97.6% | as sodium salt monohydrate. |

We claim:

1. In a process for the manufacture of a 6β-acylamino penicillanic acid antibiotic product in which 6β-amino penicillanic acid (6-APA) is reacted in an inert solvent with a silylating agent to form a silylated compound of formula (1)

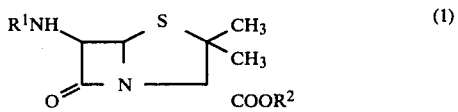

wherein $R^1$ represents a hydrogen atom or a tri($C_{1-6}$alkyl)silyl group and $R^2$ represents a tri($C_{1-6}$alkyl)silyl group and the compound of formula (I) is thereafter contacted with an acyl chloride or protected acyl chloride corresponding to the desired 6β-acylamino group, the silyl groups are cleaved with water and the desired antibiotic product is recovered, silylation being effected using a tri($C_{1-6}$alkyl)silyl urea or tri($C_{1-6}$alkyl)halosilane and the compound of formula (I) produced being reacted without intermediate isolation with the acyl chloride or protected acyl chloride, the improvement which comprises acylating in the presence of a hydrogen halide acceptor mixture comprising in excess of 0.15 up to about 3.00 moles of urea per mole of 6-APA, in excess of 0.15 up to about 1.30 moles of bis-tri($C_{1-6}$alkyl)silyl urea per mole of 6-APA, and in excess of 0.25 up to about 3.30 moles of tri($C_{1-6}$alkyl)-ammonium halide per mole of 6-APA.

2. The process of claim 1 wherein from about 0.30 to 2.60 moles of urea per mole of 6-APA, from about 0.30 to 0.90 moles of bis-tri($C_{1-6}$alkyl)silyl urea per mole of 6-APA and from about 0.50 to 3.00 moles of tri($C_{1-6}$alkyl)ammonium halide are employed.

3. The process of claim 1 wherein the bis-tri($C_{1-6}$alkyl)silyl urea and tri($C_{1-6}$alkyl)ammonium halide are formed in situ prior to the acylation reaction.

4. The process of claim 3 in which the bis-tri($C_{1-6}$alkyl)silyl urea is formed by silylation of urea with a tri($C_{1-6}$alkyl halosilane.

5. The process of claim 4 in which the 6-APA is silylated at the same time as the bis-tri($C_{1-6}$alkyl)silyl urea is formed.

6. The process of claim 1 in which mixing of all the reagents is carried out at from 0° to +20° C.

7. The process of claim 1 wherein the 6-APA is silylated using a bis-tri($C_{1-6}$alkyl)silyl urea.

8. The process of claim 1 wherein the tri($C_{1-6}$alkyl)-halosilane is trimethylchlorosilane.

9. The process of claim 8 wherein silylation is effected in the presence of a tri($C_{1-6}$alkyl)ammonium halide.

10. The process of claim 1 or claim 9 in which the tri($C_{1-6}$)alkyl ammonium halide is triethylammonium chloride.

11. The process of claim 1 wherein the solvent is methylene chloride.

12. The process of claim 1 wherein the protected acyl chloride is D(−)-α-phenylglycyl chloride hydrochloride and the antibiotic recovered is ampicillin trihydrate.

13. The process of claim 1 wherein the protected acyl chloride is D(−)-α-(4-hydroxy)phenyl-glycylchloride hydrochloride and the antibiotic recovered is amoxycillin trihydrate.

14. The process of claim 1 wherein the acyl chloride is 3-(2',6'-dichlorophenyl)-5-methyl-4-isoxazolyl chloride and the antibiotic recovered is dicloxacillin sodium salt monohydrate.

15. The process of claim 1 wherein the acyl chloride is 3-(2'-chlorophenyl)-5-methyl-4-isoxazolyl chloride and the antibiotic recovered is cloxacillin sodium salt monohydrate.

16. In a process for the manufacture of ampicillin or a salt or hydrate thereof by acylating a substantially bis-silylated derivative of 6β-aminopenicillanic acid (6-APA) with D-(−)-phenylglycyl chloride hydrochloride at a temperature from about +10° to about −35° C. in methylene chloride in the presence of a hydrogen halide acceptor, cleaving silyl groups and other protecting groups in the resultant product with water and recovering the desired ampicillin product, the improvement which comprises employing as hydrogen halide acceptor a mixture of urea, bistrimethylsilylurea and triethylammonium chloride, the amount of urea being from about 0.30 to 2.60 moles per mole of 6-APA, the amount of bistrimethylsilylurea being from about 0.30 to 0.90 moles per mole of 6-APA and the amount of triethylammonium chloride being from about 0.50 to 3.00 moles per mole of 6-APA.

17. The process of claim 16 wherein ampicillin trihydrate is recovered.

18. In a process for the manufacture of amoxycillin or a salt or hydrate thereof by acylating a substantially bis-silylated derivative of 6β-aminopenicillanic acid (6-APA) with D-(−)-(4-hydroxy)phenylglycyl chloride hydrochloride at a temperature from about +10° to about −35° C. in methylene chloride in the presence of a hydrogen halide acceptor, cleaving silyl groups and other protecting groups in the resulting product with water and recovering the desired amoxycillin product, the improvement which comprises employing as hydrogen halide acceptor a mixture of urea, bistrimethylsilylurea and triethylammonium chloride, the amount of urea being from about 0.30 to 2.60 moles per mole of 6-APA, the amount of bistrimethylsilylurea being from about 0.30 to 0.90 moles per mole of 6-APA and the amount of triethylammonium chloride being from about 0.50 up to 3.00 moles per mole of 6-APA.

19. The process of claim 18 wherein amoxycillin trihydrate is recovered.

* * * * *